(12) United States Patent
Lindstrom et al.

(10) Patent No.: US 9,526,515 B2
(45) Date of Patent: Dec. 27, 2016

(54) DEVICE FOR POSITIONING AN ULTRASOUND TRANSDUCER INSIDE A MR SCANNER

(75) Inventors: Matti Lindstrom, Espoo (FI); Gosta Ehnholm, Helsinki (FI)

(73) Assignee: Koninklijke Philips N.V., Eindhoven (NL)

( * ) Notice: Subject to any disclaimer, the term of this patent is extended or adjusted under 35 U.S.C. 154(b) by 2319 days.

(21) Appl. No.: 12/296,769

(22) PCT Filed: Mar. 16, 2007

(86) PCT No.: PCT/US2007/064184
§ 371 (c)(1),
(2), (4) Date: Oct. 10, 2008

(87) PCT Pub. No.: WO2008/048708
PCT Pub. Date: Apr. 24, 2008

(65) Prior Publication Data
US 2009/0069667 A1 Mar. 12, 2009

Related U.S. Application Data

(60) Provisional application No. 60/744,605, filed on Apr. 11, 2006.

(51) Int. Cl.
*A61B 5/05* (2006.01)
*A61B 17/225* (2006.01)
(Continued)

(52) U.S. Cl.
CPC ......... *A61B 17/2255* (2013.01); *A61B 8/4416* (2013.01); *A61B 8/00* (2013.01);
(Continued)

(58) Field of Classification Search
CPC ................. A61B 17/2255; A61B 2017/00911; A61B 8/00; A61B 8/4416; A61N 7/02
(Continued)

(56) References Cited

U.S. PATENT DOCUMENTS 4,356,577 A * 11/1982 Taylor et al. ..................... 5/608
4,435,116 A * 3/1984 Van Deberg .................. 414/728
(Continued)

FOREIGN PATENT DOCUMENTS

| JP | 62159869 A | 7/1987 |
|---|---|---|
| JP | 929681 A | 2/1997 |

(Continued)

OTHER PUBLICATIONS

Hindley et al, MRI Guidance of Focused Ultrasound Therapy of Uterine Fibroids: Early Results, AJR,183 (6): 1713-1719, Dec. 2004.*

*Primary Examiner* — James Kish
*Assistant Examiner* — Saurel J Selkin

(57) ABSTRACT

A device (16) positions an ultrasound transducer (14) for ultrasound therapy to focus a treatment beam (12) emitted by the ultrasound transducer (14) at tissue of interest. The device (16) includes at least three anchors (20) which support the ultrasound transducer (14). The device (16) further includes at least three extendable structures (24), each with a coupling (22) that supports a corresponding one of the at least three anchors (20). A drive mechanism (100) of the device (16) independently drives each of the at least three extendable structures (24) towards or away from a subject to move the ultrasound transducer (14) within at least three degrees of freedom.

1 Claim, 5 Drawing Sheets

(51) Int. Cl.
  *A61B 8/00* (2006.01)
  *A61B 17/00* (2006.01)
  *A61N 7/02* (2006.01)

(52) U.S. Cl.
  CPC ..... *A61B 34/70* (2016.02); *A61B 2017/00911* (2013.01); *A61B 2034/107* (2016.02); *A61B 2090/374* (2016.02); *A61N 7/02* (2013.01)

(58) Field of Classification Search
  USPC ........................................................ 600/411
  See application file for complete search history.

(56) References Cited

U.S. PATENT DOCUMENTS

| | | | |
|---|---|---|---|
| 4,567,780 A * | 2/1986 | Oppenlander et al. .... | 73/864.16 |
| 4,844,079 A | 7/1989 | Naser et al. | |
| 4,957,099 A | 9/1990 | Hassler | |
| 5,275,165 A * | 1/1994 | Ettinger et al. ................ | 600/411 |
| 5,443,068 A | 8/1995 | Cline et al. | |
| 5,492,122 A * | 2/1996 | Button et al. .................. | 600/411 |
| 5,626,595 A * | 5/1997 | Sklar et al. .................... | 606/170 |
| 5,740,699 A | 4/1998 | Ballantyne et al. | |
| 5,999,839 A * | 12/1999 | Hardy et al. ................... | 600/413 |
| 6,330,837 B1 * | 12/2001 | Charles et al. ............. | 74/490.06 |
| 6,506,171 B1 * | 1/2003 | Vitek et al. ........................ | 601/2 |
| 6,582,381 B1 * | 6/2003 | Yehezkeli et al. ................. | 601/2 |
| 2002/0156365 A1 | 10/2002 | Tsekos | |
| 2003/0181806 A1 | 9/2003 | Medan et al. | |
| 2005/0059878 A1 * | 3/2005 | Winter .......................... | 600/410 |
| 2005/0107702 A1 | 5/2005 | He et al. | |
| 2006/0033253 A1 * | 2/2006 | McCormick et al. ......... | 269/239 |

FOREIGN PATENT DOCUMENTS

| | | |
|---|---|---|
| JP | 2002360600 A | 12/2002 |
| WO | 8907907 A1 | 9/1989 |
| WO | 2005107870 A1 | 11/2005 |

* cited by examiner

DEVICE FOR POSITIONING AN ULTRASOUND TRANSDUCER INSIDE A MR SCANNER

CROSS REFERENCE TO RELATED APPLICATIONS

This application claims the benefit of U.S. provisional application Ser. No. 60/744,605 filed Apr. 11, 2006, which is incorporated herein by reference.

The following relates to medical imaging systems. It finds particular application to facilitating the positioning of an ultrasound transducer inside a Magnetic Resonance (MR) scanner, but is also applicable to other medical imaging modalities.

High intensity focused ultrasound (HIFU) is used to treat tumors, especially uterine fibroids. The treatment is based on warming tissue in and/or near the focus of the ultrasound beam. Sufficient warming causes cell death and subsequently a lesion in the treated volume, which often includes the tumor and some margin of healthy tissue immediately adjacent. The body then slowly absorbs the lesion, leaving the treated area tumor-free.

To achieve the foregoing, the ultrasound transducer needs to be able to be moved in a manner that focuses the beam at a desired location on the subject while avoiding exposing organs. For suitable movement, at least two translational and two angular degrees of freedom are needed. Controlling the location and extent of the warming can be facilitated via feedback from a device that can visualize both the anatomy of the treatment area and the temperature profile generated. A MR scanner can perform both functions by running dedicated sequences.

The temperature profile is obtained by locally measuring the magnetic resonance frequency of the protons in the subject. The frequency has a temperature factor that is relatively small being only one millionth of one percent per degree Celsius. The mechanisms for moving the transducer therefore are made of materials that are non-magnetic. Small amounts of any metal can be used, however, plastics and/or ceramics are mainly used. In addition the motors for powering the movements typically are placed about one meter away or more. At the same time the precision of the system is about 0.5 mm or better. This makes the system critical with respect to mechanical slack and bending.

Conventional treatment systems use positioning devices that focus the high intensity ultrasound on tissue to be treated. The transducer typically is held by a structure shaped similar to a fork that is rotated about a central axis. As a consequence, one side of the transducer is lifted while the other side of the transducer is lowered. This swiveling about the axis when lifting one side of the transducer during focusing creates problems when the transducer is to be placed relatively close to the subject, and such close positioning is often crucial when treating different size patients with tumors located at different depths. In order to make the fork stiff translation in the up-down direction is typically sacrificed, limiting the range of movements.

In one aspect, a device that positions an ultrasound transducer for ultrasound therapy to focus a treatment beam emitted by the ultrasound transducer at tissue of interest is illustrated. The device includes at least three anchors which support the ultrasound transducer and at least three extendable structures, each with a coupling that supports a corresponding one of the at least three anchors. A drive mechanism independently drives each of the at least three extendable structures towards or away from a subject to move the ultrasound transducer within at least three degrees of freedom.

One advantage includes facilitating positioning an ultrasound transducer for a high intensity focused ultrasound treatment.

Another advantage lies in freely translating the ultrasound transducer in all directions and independently inclined around two directions.

Another advantage includes translating and inclining members with minimum length relative to the amplitudes of the movements, and these members are mechanically stressed only in the lengthwise directions to minimize the amount of transducer displacement caused by elastic deformation in its suspension.

Another advantage is the translating and inclining members are made using a small amount of material to minimize their influence on the magnetic field inside the subject and on a temperature measurement.

Another advantage resides in using medical imaging to facilitate focusing the beam of the ultrasound transducer at a region of interest.

Still further advantages will become apparent to those of ordinary skill in the art upon reading and understanding the detailed description of the preferred embodiments.

The drawings are only for purposes of illustrating embodiments and are not to be construed as limiting the claims.

Figure 1:
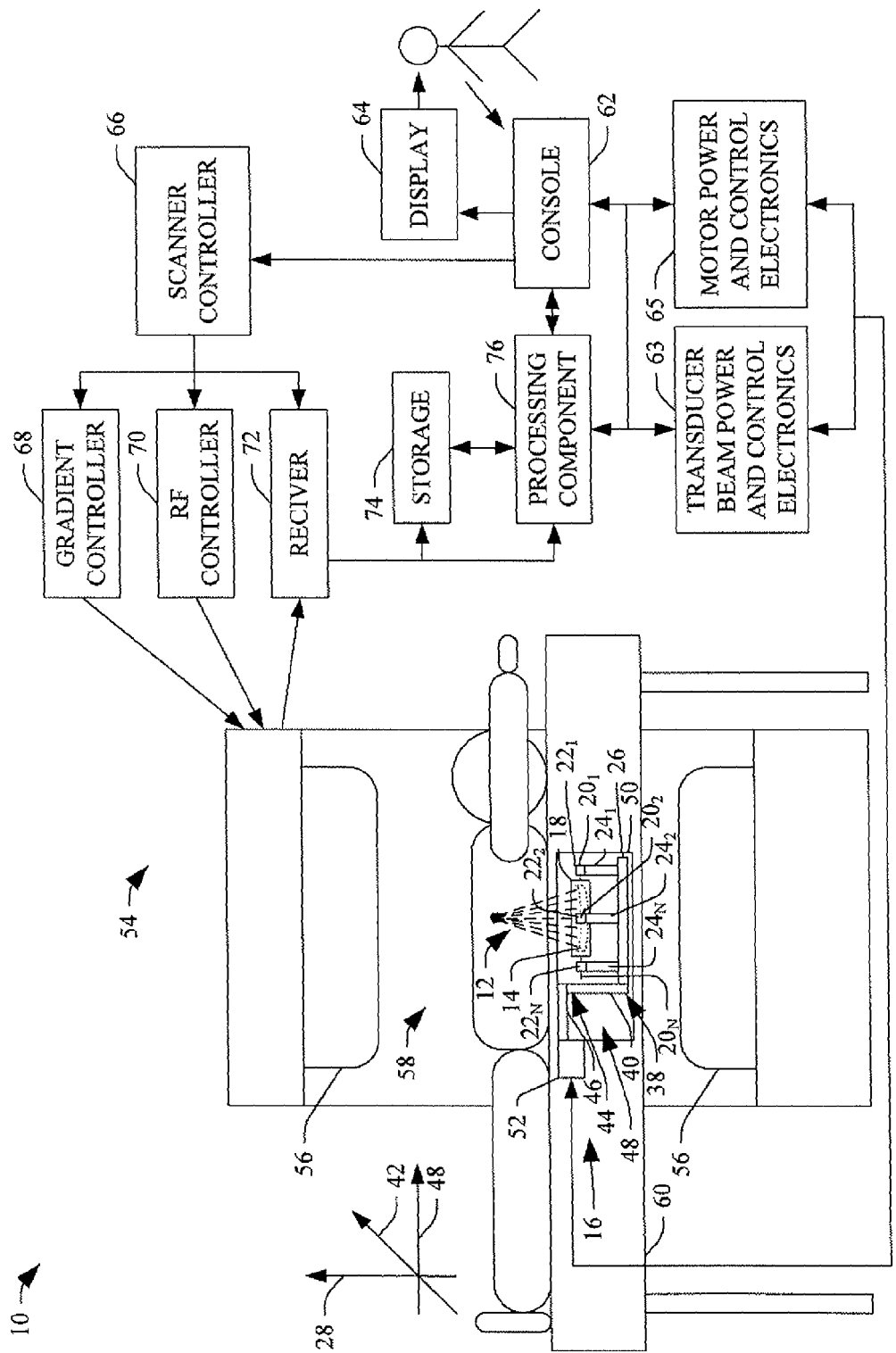
FIG. 1 illustrates a medical treatment system for treating portions of a subject/object with high intensity focused ultrasound (HIFU).

FIG. 1 illustrates a medical treatment system 10 for treating a subject/object with high intensity focused ultrasound (HIFU). A HIFU beam 12 is used to treat a region of interest within and/or the subject. The region of interest includes undesired tissue such as a tumor and some margin of healthy tissue. The HIFU beam 12 is generated and emitted by an ultrasound transducer 14, which is suitably positioned to focus the beam 12 at the region of interest 14 by a device 16 that moves the ultrasound transducer 14 through at least five degrees of freedom, at least three degrees of freedom in a direction towards and away from the subject and at least two degrees of freedom in axial and longitudinal directions with respect to the subject.

The device 16 includes a receptacle or frame 18, which supports the ultrasound transducer 14. The receptacle 18 has anchors $20_1, 20_2, \ldots, 20_N$ (collectively referred to herein as anchors 20), wherein N is a positive integer. Each of the anchors $20_1, 20_2, \ldots, 20_N$ is respectively supported by couplings $22_1, 22_2, \ldots, 22_N$ (collectively referred to herein as couplings 22). Each of the couplings $22_1, 22_2, \ldots, 22_N$ respectively reside at an end of extendible structures $24_1, 24_2, \ldots, 24_N$ (collectively referred to herein as extendible structures 24). The extendible structures 24 are moveably attached to a support plate 26 and extend and retract from the subject along a first axis 28. The couplings 22 allow the anchors 20 to translate and/or rotate therein when one or more of the extendible structures 24 extends or retracts. As the anchors 20 translate and/or rotate within their respective couplings 22, the receptacle 18 translates and/or rotates towards or away from the subject and, hence, the transducer 14 translates and/or rotates towards or away from the subject.

Figure 2:
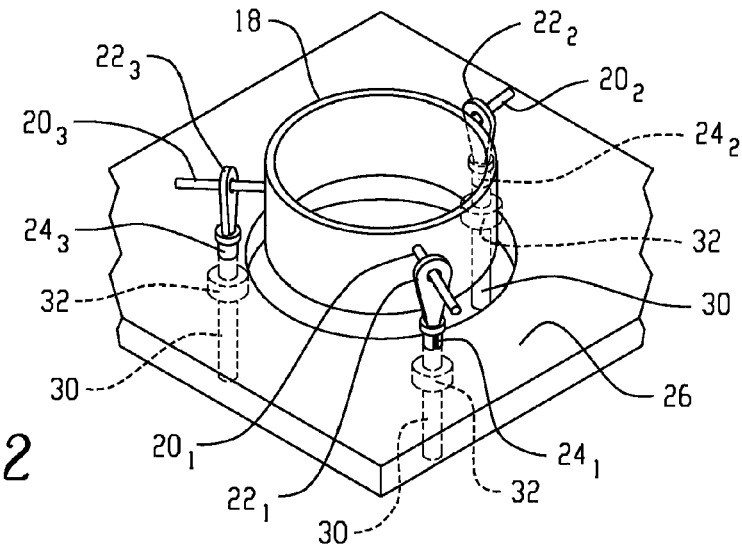
FIG. 2 illustrates a receptacle used to position an ultrasound transducer in a retracted position away from a subject.

By way of example, FIG. 2 illustrates the receptacle 18 in a retracted position away from the subject. In this example, there are three (i.e., N=3) extendible structures 24, the extendible structure $24_1$, the extendible structure $24_2$, and an extendible structure $24_3$. The extendible structures 24 are respectively associated with the couplings $22_1, 22_2,$ and $22_3$. In one instance, the couplings 22 are ball joints or the like and the anchors $20_1, 20_2,$ and $20_3$ run through the holes in the ball joints, and the extendible structures 24 are pushrods. As such, the extendible structures 24 (or pushrods) can be mounted to and actuated by lead screws 30 and corresponding lead screw nuts 32 or the like. The lead screw nuts 32 can be fixed on and rotatible about the first axis 28. Driving mechanisms X (described in detail below in connection with FIGS. 9, 10 and 11) are used to independently turn each of the lead screw nuts 32, which independently drives each lead screw 30 and extendible structure 24 along the first axis 28. In this example, the anchors 20 are positioned about 60 degrees apart from one another. However, in other embodiments, various other configurations can be used. For instance, in one alternative embodiment two of the anchors 20 are positioned about 180 degrees apart and the third anchor is positioned about 90 degrees apart from the first two anchors. Also, other extendible structures are contemplated, such as air or other fluid cylinders.

Figure 3:
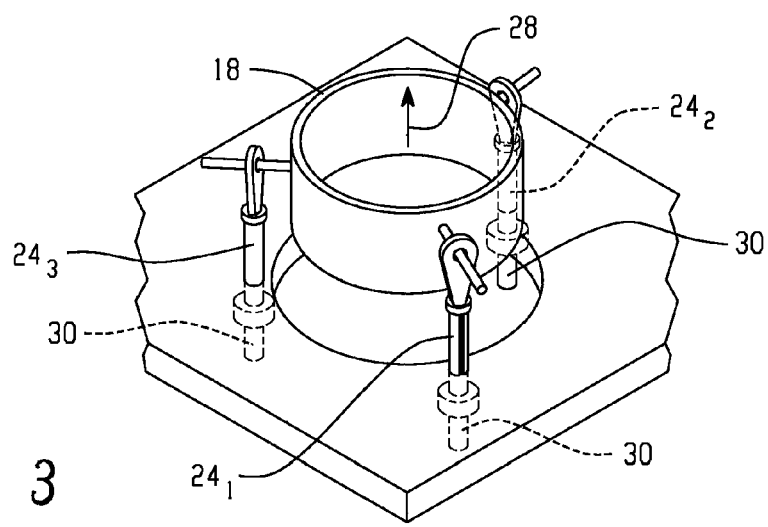
FIG. 3 illustrates a technique in which the receptacle holding the ultrasound transducer translates to re-focus the HIFU beam.
Figure 4:
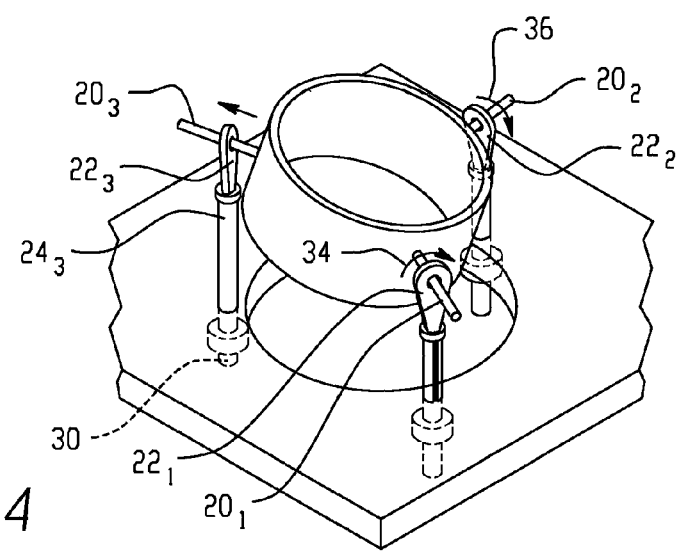
FIG. 4 illustrates a technique in which the receptacle holding the ultrasound transducer translates and rotates to re-focus the HIFU beam.

In the mode of motion illustrated in FIG. 3, the lead screws 30 are simultaneously driven at the same rate towards the subjects, which drives the extendible structures 24 in the same direction (towards the subject) at the same rate. As a result, the receptacle 18 and the ultrasound transducer 14 translate along the first axis 28 towards the subject. In FIG. 4, only the lead screw 30 associated with the extendible structure $24_3$ is driven towards the subject. The other lead screws 30 remain in a static position. As a result, the extendible structure $24_3$ extends towards the subject, the anchor $20_3$ translates through the coupling $20_3$, and the anchor $20_1$ and $20_2$ rotate (and slide a minute distance) within their respective couplings $22_1$ and $22_2$ (as illustrated at 34 and 36), which causes the receptacle 18 to rotate or tilt about the couplings $22_1$ and $22_2$. The rotation of the receptacle 18 in turn rotates the ultrasound transducer 14, which moves the focus point of the HIFU beam 12.

Returning to FIG. 2, by independently extending and/or retracting one or more of the extendible structures 24 to similar and/or different distances at similar and/or different rates, up to three degrees of freedom can be achieved and used to effectuate translational, rotational, or both translational and rotational movements of the receptacle 18 in order to move the ultrasound transducer 14 and the focal point of the ultrasound beam 12.

Returning to FIG. 1, the support plate 26 is also attached to a first end 38 of an axial motion mechanism 40, which provides translational movement of the support plate 26 along a second or transverse axis 42 in a transverse axial direction (side-to-side) with respect to the subject. A second end 44 of the axial motion mechanism 40 is attached to a longitudinal motion mechanism 46, which provides translational movement of the support plate 26 along a third or longitudinal axis 48 in a longitudinal direction with respect to the subject. The combination of the translational movements along the axes 28, 42 and 48, and the rotational movements at 34 and 36 (as illustrated in FIG. 4) provides up to five degrees of freedom in which to position the receptacle 18 to suitably focus the ultrasound beam 12.

The receptacle 18, the anchors 20, the couplings 22, the extendible structures 24, the support plate 26, the axial motion mechanism 40 and the longitudinal motion mechanism 46 reside within a cavity of a container or shell 50. Controls 52 are used to drive the extendible structures 24, the axial motion mechanism 40 and the longitudinal motion mechanism 46 in order to focus the ultrasound beam 12. The controls 52 can include mechanical components for manually focusing the beam 12 and/or electrical components for electrically focusing the beam 12.

The device 16 is used in conjunction with a scanning system 54 or other device that is capable of providing information about tissue and/or temperature profiles associated with the treatment area. Such information is used to facilitate positioning the receptacle 18 to focus the ultrasound beam 12. As illustrated in FIG. 1, the scanning system 54 can be an open Magnetic Resonance (MR) scanner. However, it is to be appreciated that other types of MR scanners and/or other imaging modalities are also contemplated herein.

In this example, the scanning system 54 includes two main magnets 56 (e.g., permanent or resistive) separated by an imaging region 58 in an open configuration. A support mechanism 60 is used to position the subject within the imaging region 58. As depicted, the device 16 resides within the support mechanism 60. The positioning of the two main magnets 56 is such that the magnets generate a magnetic field ($B_0$) in the subject. Magnetic field gradient coils (not shown, typically housed in or adjacent the main magnets) are arranged to superimpose selected magnetic field gradients on $B_0$. Such gradients include orthogonal magnetic field gradients such as x, y and/or z gradients defined within a Cartesian plane. One or more radio frequency coils (not shown, typically disposed between the gradient coils and the subject) inject radio frequency excitation pulses ($B_1$) into and/or receive resonance signals from the imaging region 58.

A console 62 and a display 64 are used to plan patient procedures (e.g., selecting imaging protocol(s), set imaging parameters, etc.), commence scanning, present reconstructed images, as well as various other features. The console 62 provides instructions to a scanner controller 66 that controls a gradient controller 68, a radio frequency (RF) source 70, and a receiver 72. The gradient controller 68 controls the magnetic field gradient coils to spatially encode the resulting magnetic resonances. The RF source 70 generates and provides the radio frequency excitation pulses ($B_1$) to the one or more radio frequency coils. During a readout phase, detection circuitry (not shown) detects the magnetic resonance signals, and the receiver 72 receives the spatially encoded magnetic resonances. The acquired spatially encoded magnetic resonances are stored in a storage component 74 and/or provided to a processing component 76, which reconstructs one or more images from the data. Raw and/or processed data (e.g., images) are displayed at the display 64, archived, filmed, conveyed for further processing, etc.

The acquired data and/or resulting images are used to focus the beam 12 on at the region of interest, which is optionally controlled from the console 62 through transducer beam power and control electronics 63 and/or motor power and control electronics 65. For example, the data and/or images provide numerical and/or graphical information about the region of interest such as the images of the treatment tissue and temperature profiles associated therewith. Thus, the data allows the operator to see the area that is being exposed to the beam 12. The operator can then, if needed, use the console 62 to control the electronics 63 and/or 65 to drive the controls 52 to reposition the receptacle 18 via one or more of the five degrees of freedom described herein to move the transducer 14 and refine the focus position of the beam 12. In one embodiment, the ultrasound beam and/or its focal spot are superimposed on the displayed image, e.g. in phantom, with a color change or shift, or the like. This provides the operator with visual feedback as the transducer is positioned. For example, the superimposed images can provide assurance that the focal spot is centered in the target tumor and that no vital or sensitive organs lie in the ultra sound beam.

Figure 5:
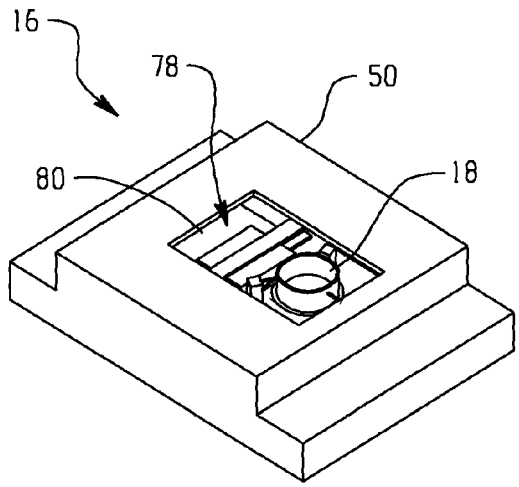
FIG. 5 illustrates an exemplary device for moving the receptacle holding the ultrasound transducer to suitably focus the HIFU beam.
Figure 6:
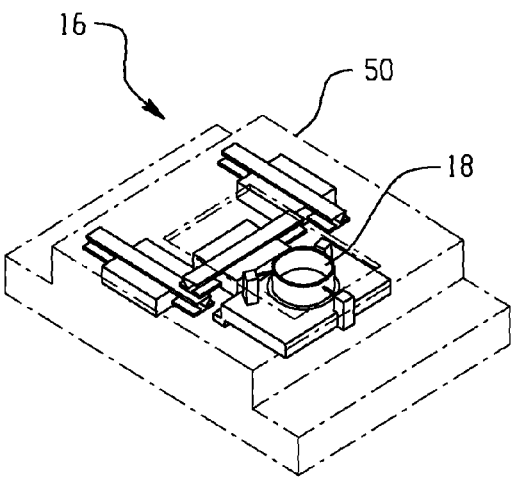
FIG. 6 illustrate an exemplary location of the receptacle within the device holding the ultrasound transducer.

Now referring to FIG. 5, an exemplary configuration of the device 16 is illustrated. The device 16 includes the container 50 with a cavity 78 in which the receptacle 18 and associated supporting and moving members are situated. The cavity 78 is filled with material (e.g., water) that is a substantially non-attenuating to the beam 12. The container 50 includes an ultrasound transmissive window 80 through which the beam 12 is directed. The window 80 is illustrated as rectangular in shaped; however, it is to be appreciated that the window 80 can be variously shaped. For example, the window 80 can alternatively be square, circular, triangular, irregular, etc. in shape. The container 50 can simply sit within the patient support 60 and/or be mounted therein through screws, clamps, Velcro™, and the like. In FIG. 6, the container 50 is illustrated as semi-transparent in order highlight the position of the receptacle 18 and its associated supporting and moving members within the container 50.

Figure 7:
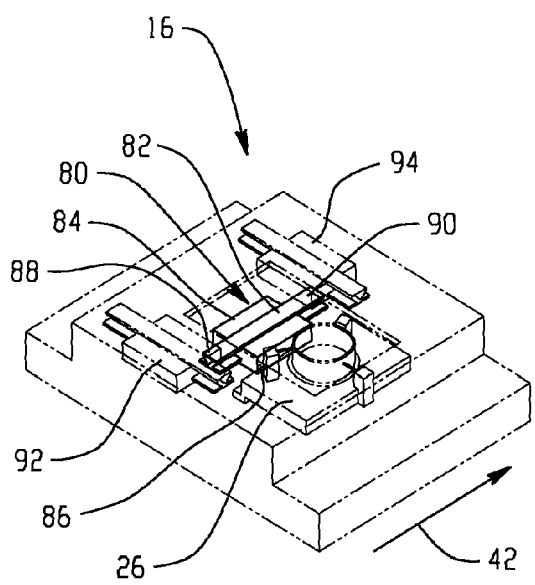
FIG. 7 illustrate an exemplary axial motion mechanism for controlling an axial position of the receptacle holding the ultrasound transducer.
Figure 8:
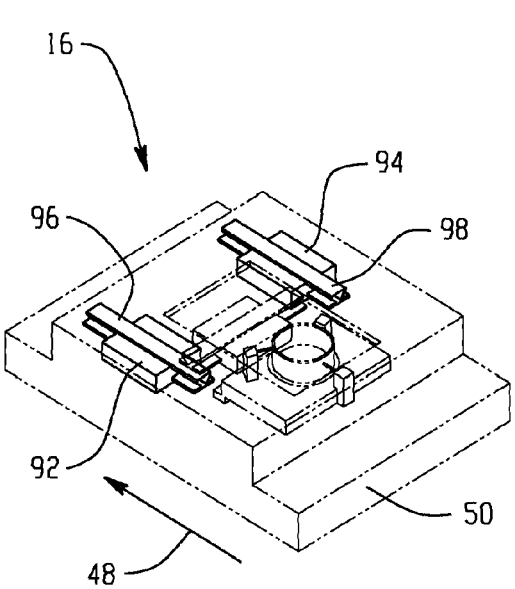
FIG. 8 illustrate an exemplary longitudinal motion mechanism for controlling a longitudinal position of the receptacle holding the ultrasound transducer.

FIGS. 7 and 8 illustrate exemplary transverse and longitudinal motion mechanisms 40 and 46, respectively. In FIG. 7, the axial motion mechanism 40, which includes a rail 82 and a carriage 84, is highlighted. The support 26 (and thus the transducer 14) is coupled to a side 86 of the carriage 84 and moves with the carriage 84 along the axis 42. The rail 82 is mounted at ends 88 and 90 to a first carriage 92 and a second carriage 94 of the longitudinal motion mechanism 46. The first and second carriages 92 and 94 are more clearly illustrated in FIG. 8. Continuing with FIG. 8, the first carriage 92 is slidably mounted to a rail 96, which is mounted the container 50, and the second carriage 94 is slidably mounted to a rail 98, which is also mounted to the container 50. Both rails 96 and 98 typically are rigidly mounted to the container 50. As discussed above, the first and second carriages 92 and 94 are respectively mounted to the rail 82, and the rail 82 moves with the first and second carriages 92 and 94 along the rails 96 and 98. Various drives, such as rack and pinion, belt, lead screw, and the like to provide transverse and longitudinal movement along the axes 42 and 48.

Figure 9:
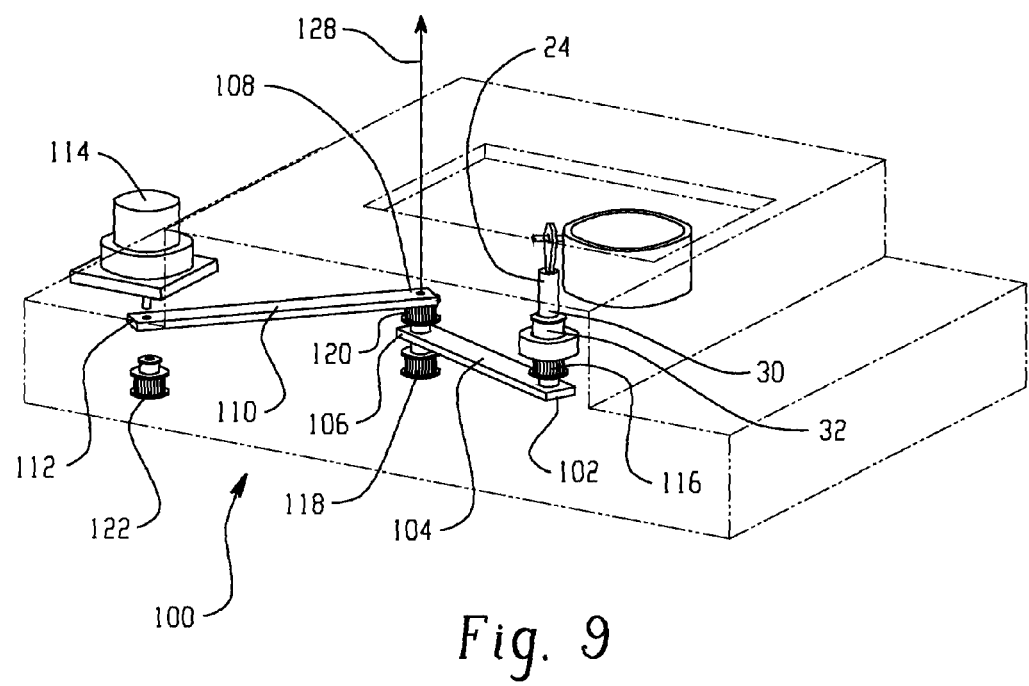
FIGS. 9, 10 and 11 illustrate an exemplary arm and wheel mechanism for driving the receptacle towards and away from the subject.
Figure 10:
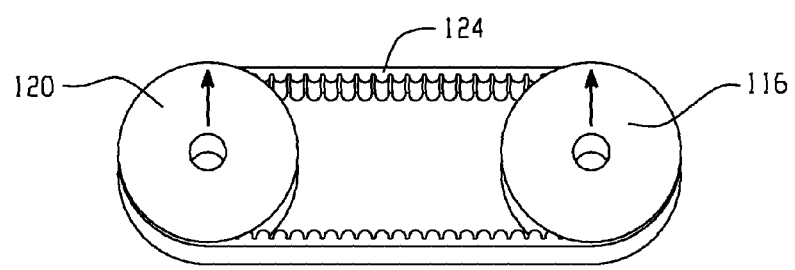
Figure 11:
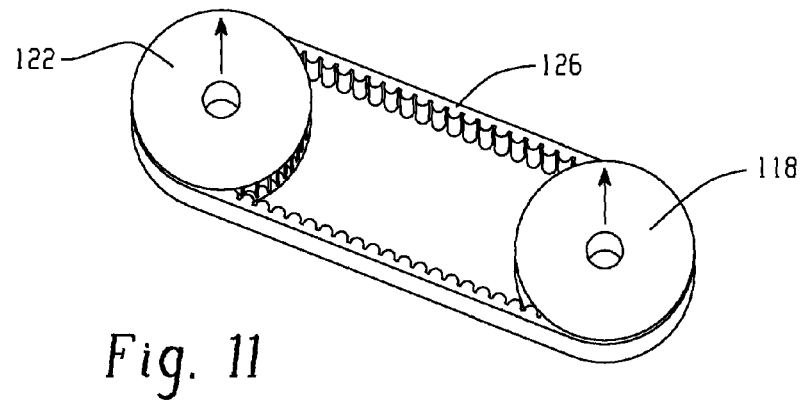

FIGS. 9, 10 and 11 illustrate an exemplary mechanism 100 that can be used to drive the extendible structures 24. As described in connection with FIG. 2 above, each extendible structure 24 can be extended and/or retracted through a lead screw assembly that includes the lead screw 30 and the lead screw nut 32. The nut 32 is fixed on and rotatible about the first axis 28 at a first end 102 of a first arm 104. A second end 106 of the first arm 104 is coupled to a first end 108 of a second arm 110, and a second end 112 of the second arm 110 is attached to a control device 114. Gears or wheels 116, 118, 120 and 122 are connected to each of the ends 102, 106, 108, and 112.

As illustrated in FIGS. 10 and 11, a belt 124 is used in conjunction with the wheels 116 and 120, and a belt 126 is used in conjunction with the wheels 118 and 122. The belts 124 and 126 are attached such that rotation of the wheel 116 translates to a corresponding rotation of the wheel 120 (and vice versa) and rotation of the wheel 118 translates to a corresponding rotation of the wheel 122 (and vice versa). The belts 124 and 126 can be toothed (as depicted), smooth, etc. and constructed from various non-magnetic materials including Kevlar™, rubber, Nylon™, etc. The rotational translation from wheel to wheel depends upon factors such as the diameter of each wheel, belt slippage, tooth cogging, hysteresis, etc. In an alternative embodiment, a rack and pinion type system can be used.

Returning to FIG. 9, the first and second arms 104 and 110 are coupled together on a similar axis 128. With this configuration, movement of the support 26, and, hence, the ultrasound transducer 14, along one or both the axes 42 and 48 can be tracked in the plane of the wheels 116-122 (within the reach of the arms) while maintaining an measurable angle of the wheels 116-122. Using the same size wheels with non-slipping belts allows an absolute angle to be measured. The control device 114 turns the wheel 122, which turns the belt 124 of arm 110, which in turn causes the wheel 120 to rotate. The wheels 120 and 118 are coupled such that rotating either wheel will cause the other wheel to rotate. Rotation of the wheel 118 turns the belt 126 of arm 104, which in turn causes the wheel 116 to rotate. The rotation of the wheel 116 turns the lead screw nut 32, which drives the lead screw 30 and extendible structure 24 along the axis 28 towards or away from the subject. Although FIG. 9 only shows one arm/wheel/belt assembly, similar assemblies can be used to control each of the other extendible structures 24.

It is to be appreciated that the components of the device 26 can be designed for use inside a MR or other type of medical imaging scanner. In addition, the components can be constructed from available or readily manufactured from non-magnetic materials.

Figure 12:
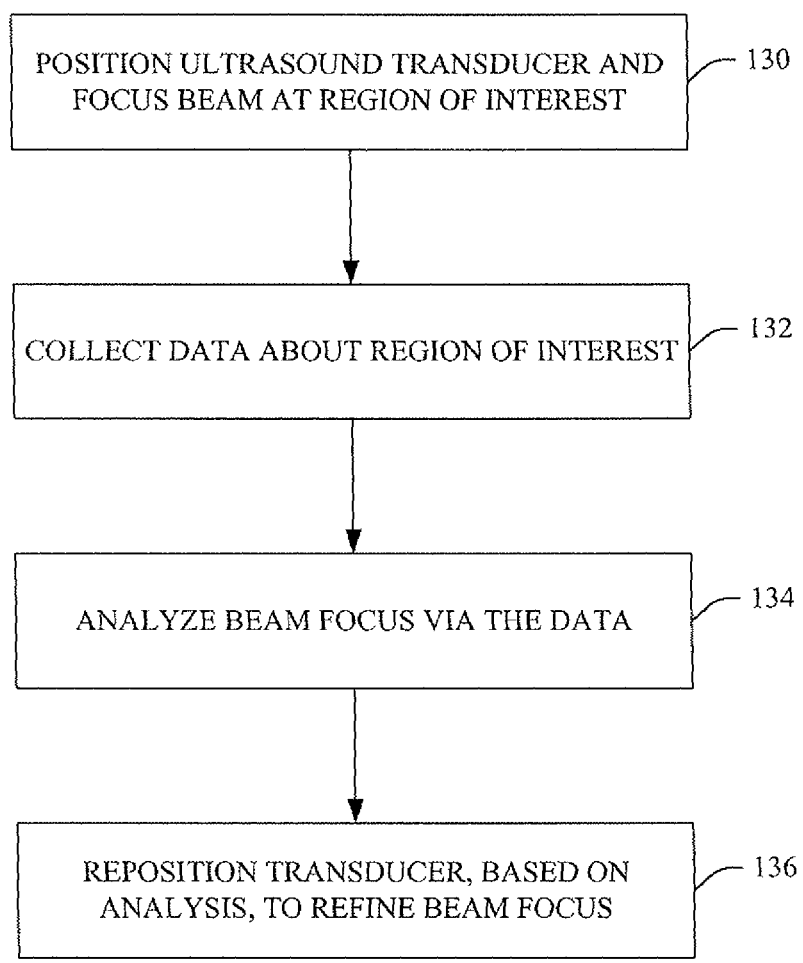
FIG. 12 illustrates a method for positioning an ultrasound transducer used to treat portions of a subject/object with high intensity focused ultrasound (HIFU).

FIG. 12 illustrates a method for positioning an ultrasound transducer used to treat portions of a subject/object with high intensity focused ultrasound (HIFU). The method includes using a device (e.g., the device 16) that provides at least three degrees of freedom for moving an ultrasound transducer (e.g., the transducer 14) towards or away from a subject through a translation and/or two rotational motions in connection with a medial imaging system (e.g., the MR scanner 54). The device also provides at least two degrees for moving the ultrasound transducer axially and longitudinally with respect to the subject.

At reference numeral 130, the device 16 suitably positions the ultrasound transducer 14 to an initial position for treating a particular region in the subject. The ultrasound transducer 14 is activated and an ultrasound beam 12 is directed into the subject. At 132, the imaging system 54 is used to collect data representative of tissue in the treatment region and a temperature profile of the treatment region. Optionally, the temperature profiles are superimposed on the displayed image, e.g. by temperature depending shading. At 134, the operator determines from the data whether the position of the ultrasound transducer should be refined to further focus the beam at the treatment area. Assuming the operator desires to refine the position of the ultrasound transducer, at 136, the operator uses the controls 52 to extend or retract one or more of the extendible structures 24, as describe above, for example, through the arm and wheel system 100. Such movement results in translation and/or rotational movement of the beam to move the focus depth of the beam. Optionally, the operator uses the controls 52 to move the support 26 in a transverse and/or longitudinal direction with respect to the patient to move the beam to move a different transverse and/or longitudinal location. The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A medical treatment system comprising: a magnetic resonance medical imaging system including:
   a main magnet that generates a magnetic field within an imaging region of the medical imaging system,
   magnetic field gradient coils that superimpose selected magnetic field gradients on $B_0$, the magnetic field gradient coils are controlled by a gradient controller,
   one or more radio frequency coils that inject radio frequency excitation pulses produced by radio frequency (RF) source into the imaging regions,
   a receiver that receives spatially encoded magnetic resonances,
   a console for controlling the magnetic resonance imaging system, and
   a display on which the diagnostic images are displayed;
   an ultrasound transducer which emits a treatment beam, the ultrasound transducer being mounted in a subject support; and
   a device for positioning the ultrasound transducer for ultrasound therapy to locus the treatment beam emitted by the ultrasound transducer at tissue of interest of the subject in the examination region for an ultrasound therapy medical treatment, the device including at least the following components:
   at least three anchors which support the ultrasound transducer;
   at least three extendable structures, each with a coupling that supports a corresponding one of the at least three anchors; and
   a drive mechanism which independently drives each of the at least three extendable structures towards or away from a subject to move the ultrasound transducer within at least three degrees of freedom;
   the components of the device being constructed from non-magnetic materials; and
   a processing unit which superimposes at least a focal spot at which the treatment beam is focused on the diagnostic image;
   wherein the extendable structures are rigid and extend along axes which intersect the subject and the drive mechanism includes:
   a lead screw connected with and extending parallel to the axes of each of the extendable structures; and
   a lead screw nut which rotates around each lead screw to extend or retract the associated extendable structure towards or away from the subject,
   wherein each lead screw nut is turned via an arm and wheel mechanisms.

* * * * *